United States Patent [19]
Miyakawa et al.

[11] Patent Number: 6,120,444
[45] Date of Patent: Sep. 19, 2000

[54] NONCONTACT TONOMETER CAPABLE OF MEASURING INTRAOCULAR TENSION BY OPTICALLY DETECTING DEFORMATION OF CORNEA CAUSED BY AIR CURRENT

[75] Inventors: Kazuhiro Miyakawa; Toshifumi Mihashi; Isao Minegishi, all of Tokyo, Japan

[73] Assignee: Kabushiki Kaisha TOPCON, Tokyo, Japan

[21] Appl. No.: 09/324,838

[22] Filed: Jun. 3, 1999

[30] Foreign Application Priority Data

Jun. 5, 1998 [JP] Japan .................................. 10-157945
Sep. 3, 1998 [JP] Japan .................................. 10-248920

[51] Int. Cl.$^7$ ........................................................ A61B 3/16
[52] U.S. Cl. .......................................... 600/401; 351/211
[58] Field of Search .................................... 351/211, 212, 351/208, 221, 246, 209; 600/398, 399, 401, 402

[56] References Cited

U.S. PATENT DOCUMENTS

| | | | |
|---|---|---|---|
| 5,682,224 | 10/1997 | Takagi et al. | 351/208 |
| 5,727,551 | 3/1998 | Takagi | 600/399 |
| 5,776,061 | 7/1998 | Hayafuji | 600/401 |
| 5,841,502 | 11/1998 | Miwa | 351/209 |

FOREIGN PATENT DOCUMENTS

08275920  10/1996  Japan .

*Primary Examiner*—George Manuel
*Attorney, Agent, or Firm*—Jacobson, Price, Holman & Stern, PLLC

[57] ABSTRACT

A noncontact tonometer comprises an air current blowing means for blowing an air current against an eye, a cornea deformation measuring means for optically measuring a change in the shape of the cornea caused by the air current blowing means, and an arithmetic means capable of calculating the intraocular tension of the eye on the basis of the change in the shape of the cornea. Since the intraocular tension of the eye can be calculated on the basis of the change in the shape of the cornea by the arithmetic means, the pressure of the air current blown against the eye need not be high, which lightens load on the subject.

7 Claims, 8 Drawing Sheets

NONCONTACT TONOMETER CAPABLE OF MEASURING INTRAOCULAR TENSION BY OPTICALLY DETECTING DEFORMATION OF CORNEA CAUSED BY AIR CURRENT

BACKGROUND OF THE INVENTION

1. Field of the Invention

The present invention relates to a noncontact tonometer that blows an air current against an eye and measures optically a deformation of its cornea caused by the air current to determine the intraocular tension of the eye by noncontact measurement.

2. Description of the Related Art

Conventionally there is widely known a noncontact tonometer that measures the intraocular tension of an eye by a noncontact measuring method. In the method, first, the eye is blown by an air pulse to be a state of the applanation of its cornea. The state of the applanation means that the top portion of the cornea is deformed to be flat. Hereinafter, the word, "applanation", means the same meaning. The state of the applanation of the cornea, second, is detected optically in the method so that the intraocular tension of the eye is measured.

Figure 1:
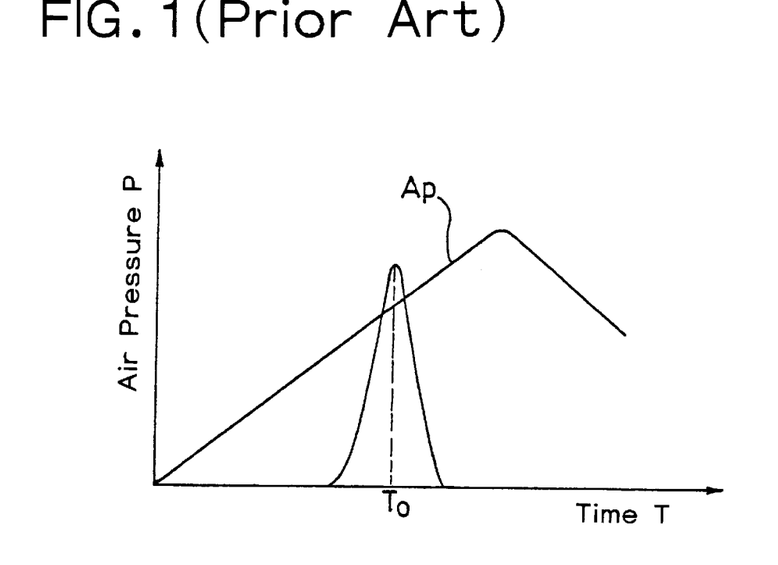
FIG. 1 is a graph of assistance in explaining the relation between the variation of the blowing pressure of an air pulse and intraocular tension.
Figure 2:
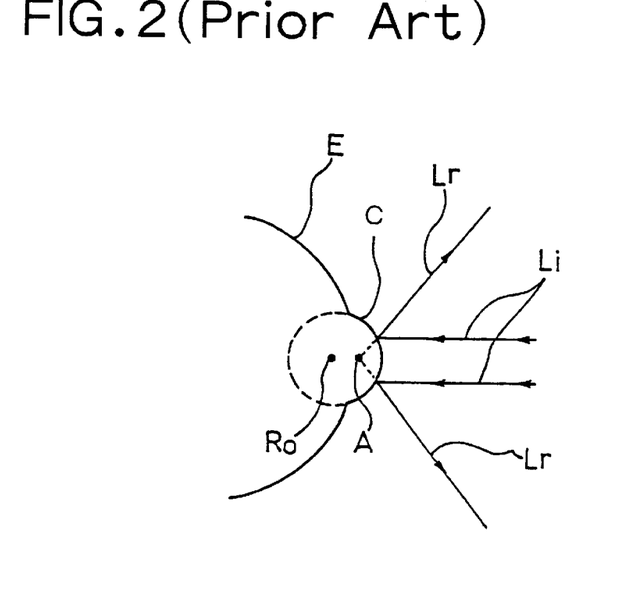
FIG. 2 is a diagrammatic view of assistance in explaining the behavior of light beams for detecting the applanation of the cornea in a state where any air pulse is not blown against the eye.

More specifically, an air pulse Ap whose pressure to the eye increases in proportion to time as shown in FIG. 1 is blown against the eye, and the eye is irradiated with parallel light beams Li as shown in FIG. 2.

A cornea C in an ordinary state has a spherical surface before being blown with an air pulse. Therefore, when the cornea C in the ordinary state is irradiated with the incident light beams Li, reflected light beams Lr travel as if the reflected light beams Lr are radiated from a point A at a distance equal to half the radius of curvature of the cornea C forward along the optical axis of the eye E from the center Ro of curvature of the cornea C.

Figure 3:
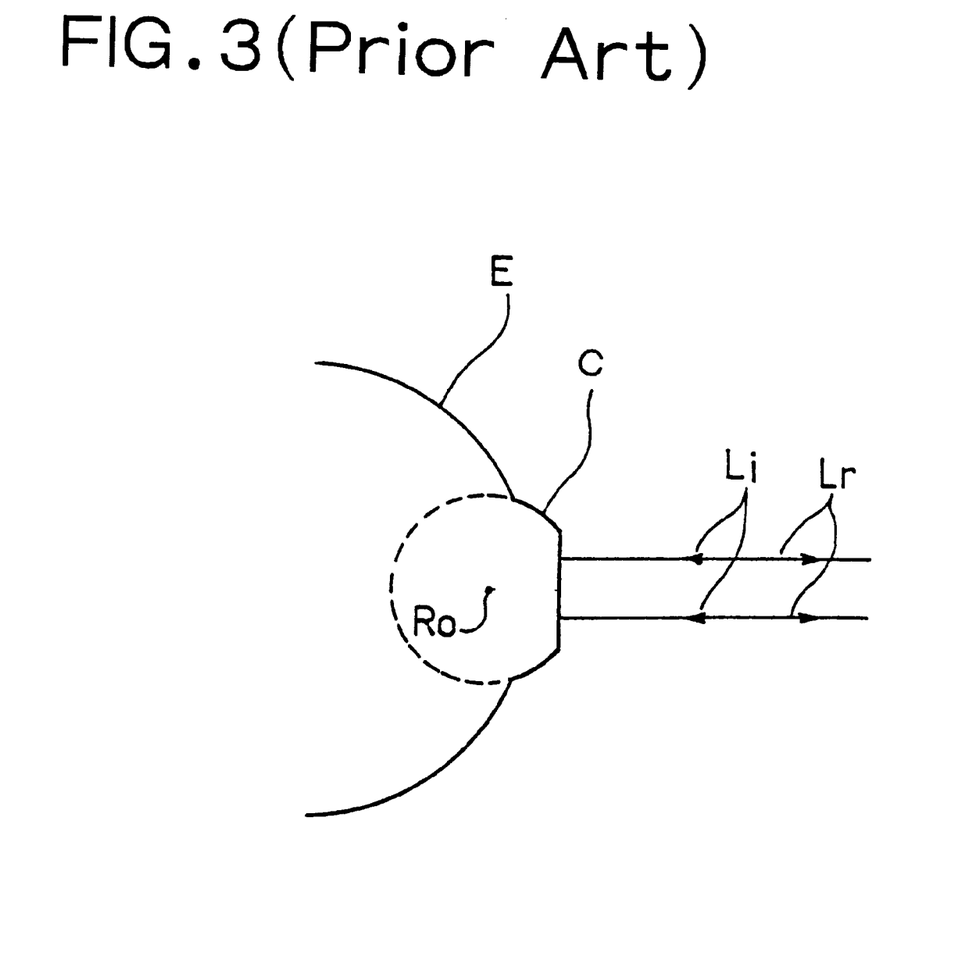
FIG. 3 is a diagrammatic view of assistance in explaining the behavior of light beams for detecting the applanation of the cornea in a state where an air pulse is blown against the eye.

In a state where the cornea C is flattened as shown in FIG. 3 by the air pulse, the reflected light beams Lr travel in parallel to each other. The reflected light beams Lr are detected by a light receiving device disposed so that the intensity of light fallen thereon is a maximum when the cornea C is flattened. Time T0 (FIG. 1) elapsed before the intensity of received light increases to the maximum, i.e., time elapsed before the cornea C is flattened, is measured, and intraocular tension is calculated on the basis of the time T0.

This noncontact tonometer is unable to measure the intraocular tension of the eye unless the eye is flattened. Therefore, the pressure of the air pulse must inevitably be high enough to achieve the applanation of the eye. The air pulse of such a high pressure is unpleasant to the subject. The air pulse generates a large sound to startle the subject.

SUMMARY OF THE INVENTION

An object of the present invention is to provide a noncontact tonometer capable of measuring the intraocular tension of the eye by blowing an air current of the least necessary pressure against the eye and of lightening load on the subject.

With the foregoing object in view, according to a first aspect of the present invention, there is provided a noncontact tonometer in which a light pattern projecting system projects a light pattern on the eye, a light receiving system receives a reflected light pattern reflected from the cornea, and an arithmetic means calculates the intraocular tension of the eye on the basis of a change in an image of the light pattern formed on the light receiving system.

There is obtained an effect that an air current of the least necessary pressure is used, and load on the subject can be lightened.

According to a second aspect of the present invention, there is provided a noncontact tonometer in which an arithmetic means calculates the intraocular tension of the eye on the basis of degree of deformation of an image of a light pattern in a predetermined time.

The effect of the noncontact tonometer in the second aspect of the present invention is the same as that of the noncontact tonometer in the first aspect of the present invention.

According to a third aspect of the present invention, there is provided a noncontact tonometer in which a light pattern consists of a plurality of concentric rings having their centers on the optical axis of the eye.

The intraocular tension can easily be determined through the analysis of the change of the light pattern consisting of the plurality concentric rings.

According to a fourth aspect of the present invention, there is provided a noncontact tonometer in which an air blowing means is capable of blowing an air current of a pressure lower than that necessary for the applanation of the cornea of the eye.

There is obtained an effect that an air current of the least necessary pressure is used, and load on the subject can be lightened.

According to a fifth aspect of the present invention, there is provided a noncontact tonometer in which a light receiving system is telecentric with respect to the side of the object.

An image of a Placido's ring is formed in the same size on a light receiving means regardless of slight deviation of working distance.

According to a sixth aspect of the present invention, there is provided a noncontact tonometer in which a memory stores reference data to be used for determining the intraocular tension of the eye, and an arithmetic means compares an image of a pattern formed by a light receiving system with the reference data and calculates the intraocular tension of the eye on the basis of the results of comparison.

The noncontact tonometer is able to determine the intraocular tension easily.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

Noncontact tonometers in preferred embodiments according to the present invention will be described hereinafter with reference to the accompanying drawings.

(1) First Embodiment

Figure 4:
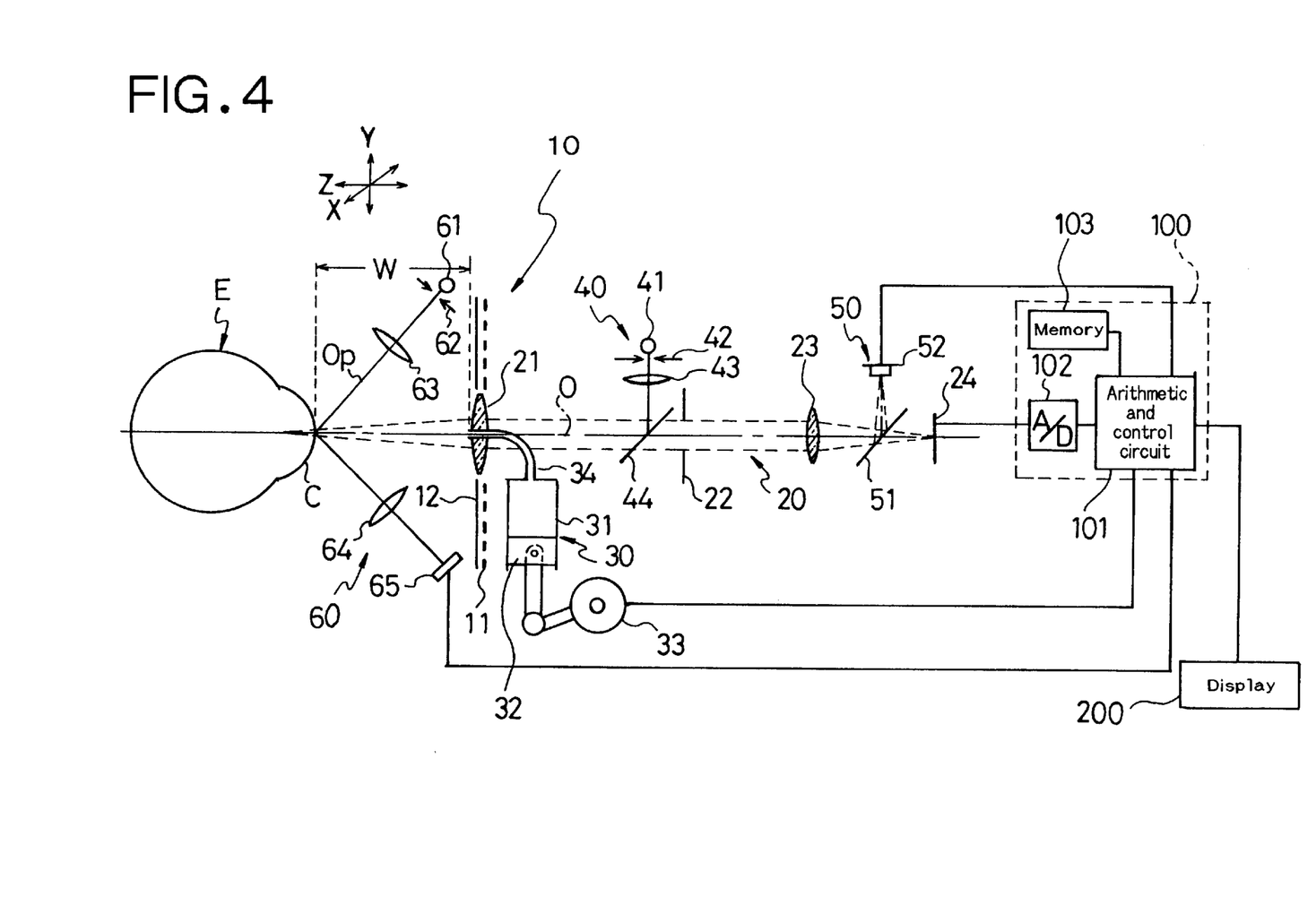
FIG. 4 is a block diagram of an optical system and a control system included in a noncontact tonometer in a first embodiment according to the present invention.

Referring to FIG. 4, a noncontact tonometer in a first embodiment according to the present invention comprises, as principal components, a Placido's ring pattern projecting system (light pattern projecting system) 10, an observation optical system 20, an air jetting system (air blowing means) 30, an XY alignment light projecting optical system 40, an XY alignment detecting optical system 50, a working distance measuring system 60, a control system 100 and a display 200.

Placido's Ring Pattern Projecting System 10

Figure 5:
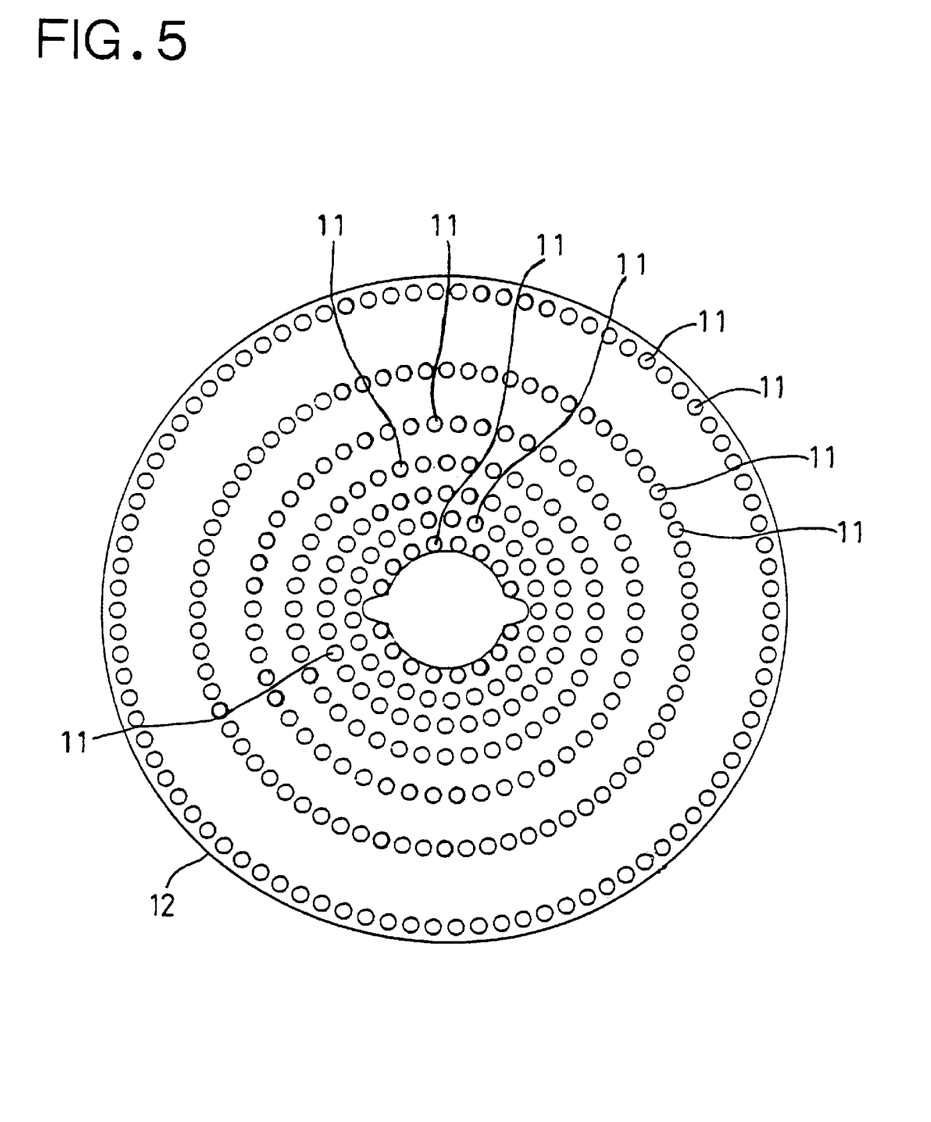
FIG. 5 is a diagrammatic view of assistance in explaining the relation between a diffusing plate shown in FIG. 4, and light-emitting diodes.
Figure 6:
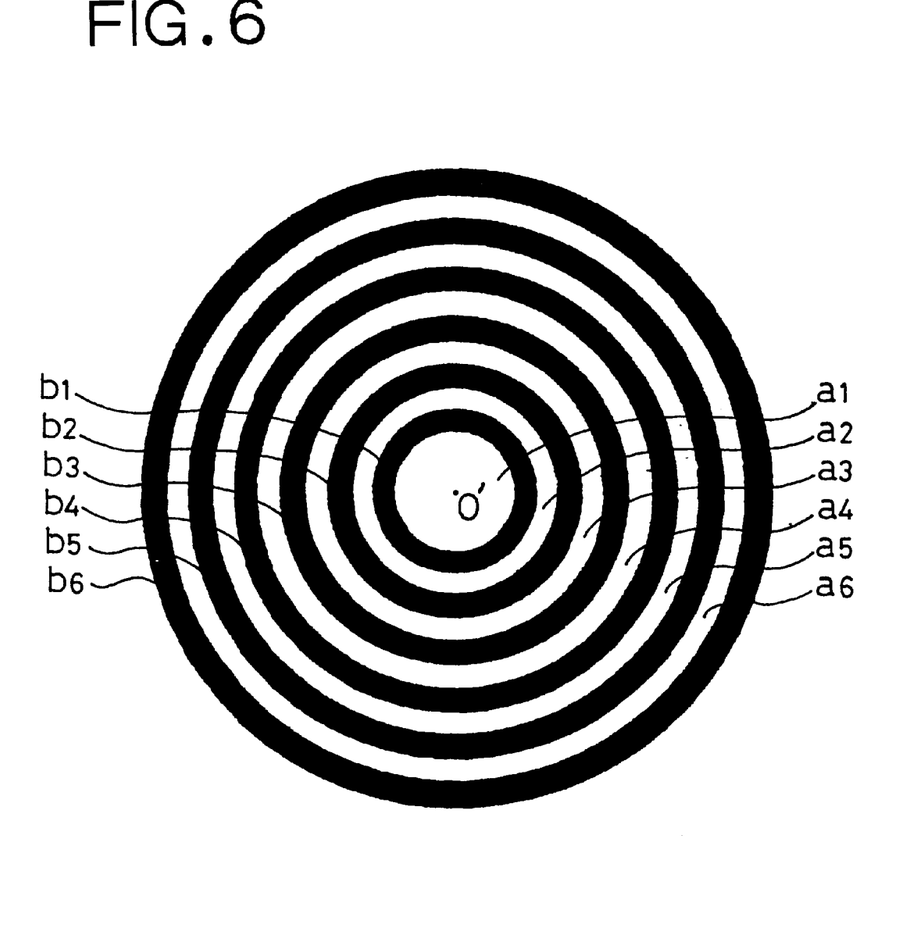
FIG. 6 is a view of assistance in explaining a pattern formed on the diffusing plate shown in FIG. 4.

Referring to FIG. 4, the Placido's ring pattern projecting system 10 projects a light pattern consisting of a plurality of concentric rings on the cornea C of the eye E. The Placido's ring pattern projecting system 10 comprises a plurality of light-emitting diodes 11 arranged on concentric circles as shown in FIG. 5, and a diffusing plate 12 provided with a ring pattern consisting of a plurality of concentric rings as shown in FIG. 6. The Placido's ring pattern projecting system 10 may be similar in configuration to a Placido's pattern projecting system disclosed in JP-A No. 8-275920. In FIG. 6, indicated at a1 to a6 are optically transparent parts and at b1 to b6 are optically opaque parts.

Observation Optical System 20

The observation optical system 20 is used for observing the anterior segment of the eye E, and observing and recording an image of a Placido's ring. The observation optical system 20 comprises an objective lens 21, a telecentric diaphragm 22, an image forming lens 23 and a CCD (light receiving means) 24. The optical axis O of the observation optical system 20 passes the center O' of the pattern of the plurality of rings of the Placido's ring pattern projecting system 10.

The CCD 24 is disposed so as to be optically conjugate with the focal plane of the cornea C of the eye E disposed at a proper working distance W with respect to the objective lens 21 and the image forming lens 23.

Illuminating light beams projected by the Placido's ring pattern projecting system 10 are reflected by the cornea C, and a virtual image of the Placido's ring is formed near the focal plane F of the cornea C. Since the observation optical system 20 is telecentric with respect to the side of the object, the image of the Placido's ring is formed on the CCD 24 in the same size even if the actual working distance is slightly different from the proper working distance W.

Air Jetting System 30

The air jetting system 30 jets an air pulse whose pressure to the eye E varies in proportion to time. The air jetting system 30 comprises a cylinder 31, a piston 32, a solenoid 33 for driving the piston 32 and an orifice pipe 34. As shown in FIG. 4, the orifice pipe 34 has one end part penetrating a central part of the objective lens 21 and the other end part connected to a closed end of the cylinder 31. The piston 32 is driven to compress air in the cylinder 31, and compressed air is jetted toward the cornea C of the eye E.

The present invention measures intraocular tension on the basis of a change in the shape of the image of the Placido's ring before and after an air pulse is begun to be jetted against the cornea C. Therefore the applanation of the eye E is unnecessary, and the intensity of the air pulse may be lower than that of an air pulse used in a conventional noncontact tonometer. For example, an air pulse of 5 mmHg in peak pressure is sufficient for measurement. A conventional noncontact tonometer needs an air pulse of about 15 mmHg in peak pressure.

XY Alignment Light Projecting Optical System 40

The XY alignment light projection optical system 40 projects a position indicating light beam on the eye E to examine the position of the eye E relative to the optical axis O with respect to vertical direction (direction along the Y-axis), and horizontal direction (direction along the X-axis). The XY alignment light projecting optical system 40 comprises a light source 41, a pinhole plate 42, a collimator lens 43, a semitransparent mirror 44 and the objective lens 21. The pinhole plate 42 is disposed at the front focal point of the collimator lens 43. A position indicating light beam, i.e., a beam of parallel light beams, is projected through the objective lens 21 on the eye E.

XY Alignment Detecting Optical System 50

The XY alignment detecting optical system 50 detects the positional relation between the eye E and the optical axis O with respect to directions along the X-axis and the Y-axis. The XY alignment detecting optical system 50 comprises the objective lens 21, the image forming lens 23, a semitransparent mirror 51 and a light receiving device 52. The light receiving device 52 is a photodiode capable of measuring the intensity of incident light. The photodiode receives the alignment index light beam projected by the XY alignment light projecting optical system 40 and reflected by the cornea C, and determines the position of the eye E relative to the optical axis O with respect to directions along the X-axis and the Y-axis on the basis of the intensity of the incident light. The light receiving device 52 may be a PSD (position sensitive device) capable of determining the centroid of the intensity of the incident light.

Working Distance Measuring System 60

The working distance measuring system 60 comprises a light source 61, a slit plate 62, a collimator lens 63, a condenser lens 64 and a light receiving device 65. Light emitted by the light source 61 travels through the slit of the slit plate 62 and is collimated by the collimator lens 63 in a collimated working distance measuring light beam. The working distance measuring light beam falls obliquely on the eye E. The working distance measuring light beam reflected by the cornea C of the eye E travels through the condenser lens 64 and falls on the light receiving device 65. The light receiving device 65 is, for example, a line sensor capable of supplying a position signal corresponding to the position of the light beams thereon. The light receiving device 65 supplies a signal corresponding to the distance of the eye E from the objective lens 21. A position on the light receiving device 65 at which the working distance measuring light beam reflected from the cornea C falls corresponds to the distance between the cornea C and the objective lens 21.

Control System 100

The control system 100 comprises an arithmetic and control circuit 101, an A/D converter 102 and a memory 103. A detection signal supplied by the light receiving device 52 is given to the arithmetic and control circuit 101. The solenoid 33 is controlled for operation by the arithmetic and control circuit 101.

Figure 7:
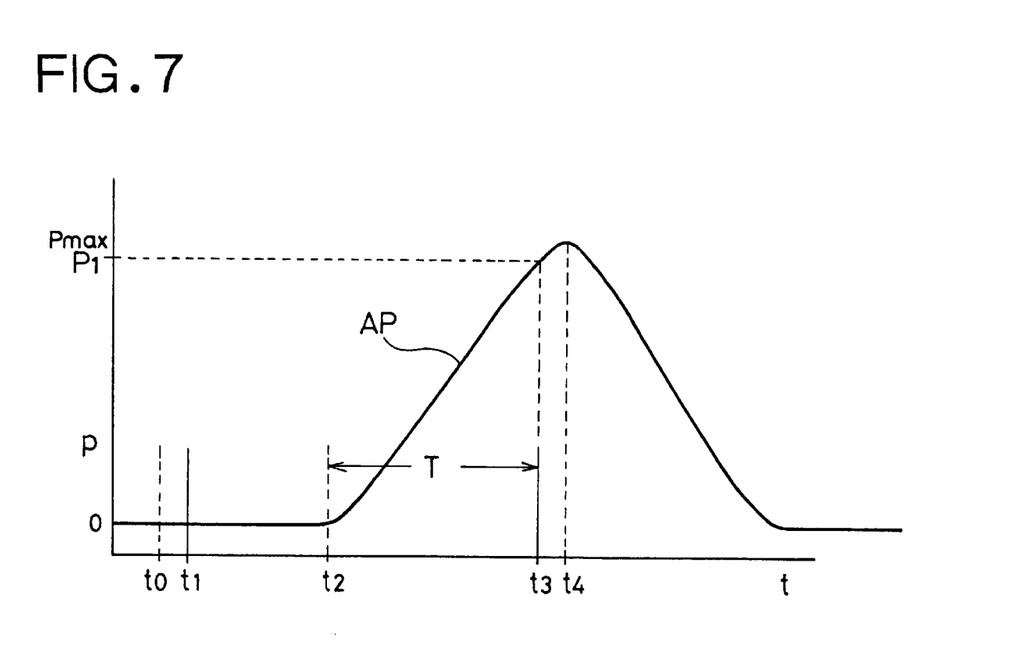
FIG. 7 is a graph of assistance in explaining the relation between the photographing operation of the noncontact tonometer shown in FIG. 4 and an air pulse.

The arithmetic and control circuit 101 transfers image data obtained by the A/D conversion of information about an image of the Placido's ring provided by the CCD 24 by the A/D converter 102 to the memory 103 at predetermined time. For example, first image data transfer operation for transferring image data is executed at time t1 between time t0 when an alignment completion signal is supplied and time t2 when an air jetting operation is started. A second image data transfer operation is executed at time t3 before time t4 when the pressure of an air pulse reaches the maximum and T seconds after the time t2 as shown in FIG. 7. Image data thus transferred thereto is stored in the memory 103.

Figure 8:
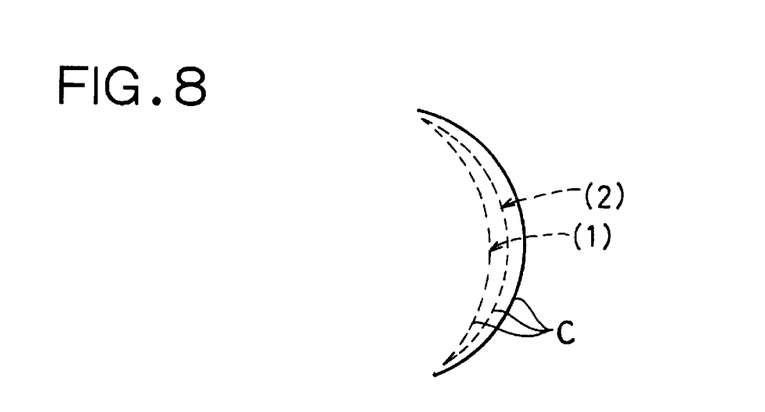
FIG. 8 is a view of assistance in explaining the effect of the air pulse blown against the eye by the noncontact tonometer shown in FIG. 4.
Figure 9A:
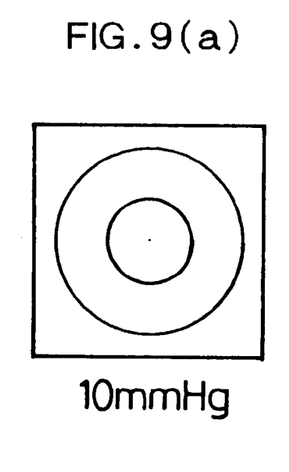
FIGS. 9(a), 9(b), 9(c) and 9(i) are views of patterns representing the relation between the deformation of the cornea of the eye shown in FIG. 7 and intraocular tension.
Figure 9B:
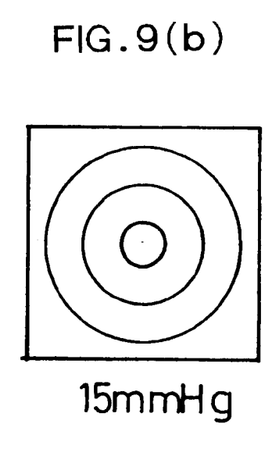
Figure 9C:
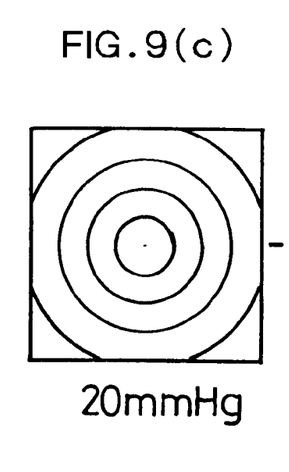
Figure 9I:
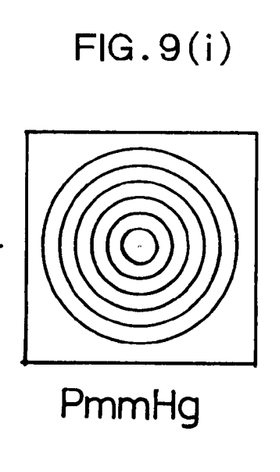

The degree of deformation of the cornea C at time T seconds after the time t2 when the air jetting operation is started when the intraocular tension is 10 mmHg and that of the same at time T seconds after the time t2 when the air jetting operation is started when the intraocular tension is 15 mmHg are greatly different from each other. FIG. 8 shows a conceptional illustration of the deformation of the cornea C. In FIG. 8, a curve (1) represents a degree of deformation of the cornea C at time t seconds after the start of the air jetting operation for jetting an air pulse of 5 mmHg in pressure when the intraocular tension is 10 mmHg, and a curve (2) represents a degree of deformation of the cornea C at time T seconds after the start of the air jetting operation for jetting an air pulse of 5 mmHg in pressure when the intraocular tension is 15 mmHg. As is obvious from FIG. 8, the higher the intraocular tension, the more difficult is the cornea C to be depressed. Therefore, the higher the intraocular tension, the less is the deformation of the ring pattern formed on the cornea C. Accordingly, the intraocular tension of the eye E can be determined through the analysis of the deformation of the ring pattern.

The memory 103 stores reference image data on the images of the Placido's ring pattern formed when an air pulse of 5 mmHg in peak pressure (hereinafter referred to as "5 mmHg air pulse") is jetted against eyes respectively having known intraocular tensions. FIGS. 9(a) to 9(i) show reference image data on images of the Placido's ring pattern when an 5 mmHg air pulse is jetted against eyes respectively having intraocular tensions of 10+i mmHg (i=1, 2, 3, ... and 10) by way of example.

The arithmetic and control circuit 101 compares measured image data with the reference image data, and selects a reference image data most analogous with the measured image data. An intraocular tension corresponding to the selected reference image data is displayed on the display 200. The arithmetic and control circuit 101, the CCD 24 and the air jetting system (air blowing means) 30 constitute a cornea deformation measuring means.

The operation of the noncontact tonometer will be described below.

A light source, not shown, for illuminating the anterior segment of the eye E is turned on to illuminate the anterior segment of the eye E. A reflected light beam reflected from the anterior segment of the eye E travels through the objective 21, the semitransparent mirror 44, the telecentric diaphragm 22, the image forming lens 23 and the semitransparent mirror 51 and fall on the CCD 24. Thus, an image of the anterior segment of the eye E is formed on the CCD 24 and the CCD 24 supplies an image signal. The image signal is transferred through the A/D converter 102 and the arithmetic and control circuit 101 to the display 200. The display 200 displays the image of the anterior segment of the eye E.

The light source 41 for XY alignment and the light source 61 for working distance measurement are turned on. XY alignment light emitted by the light source 41 travels through the semitransparent mirror 44 and the objective lens 21, falls on the eye E, and is reflected by the cornea C of the eye E. The reflected XY alignment light travels through the objective lens 21, the semitransparent mirror 44, the telecentric diaphragm 22, the image forming lens 23 and the semitransparent 51 and falls on the light receiving device 52.

Working distance measuring light emitted by the light source 61 travels through the slit of the slit plate 62, and is collimated by the collimator lens 63 in a collimated slit beam. The collimated slit beam falls on the cornea C of the eye E, is reflected by the cornea C, and the reflected collimated slit beam travels through the condenser lens 64 and falls on the light receiving device 65.

Image signals supplied by the light receiving devices 52 and 65 are given to the arithmetic and control circuit 101. The arithmetic and control circuit 101 makes the display 200 superpose a bright spot, not shown, on the image of the anterior segment displayed on the display 200 at a position represented by the image signal provided by the light receiving device 52. A joystick, not shown, is operated for motions in directions along the X-axis and the Y-axis to make the bright spot displayed on the display 200 coincide with the optical axis O of the noncontact tonometer. The joystick is operated for fore-and-aft motion to measure working distance W, i.e., the distance between the objective lens 21 and a top point of the cornea C, by the agency of the light receiving device 52 and the arithmetic and control circuit 101 to position the cornea C properly with respect to directions along the optical axis of the noncontact tonometer (Z-axis).

XY alignment using the bright spot and working distance adjustment using the output signal of the light receiving device 65 can be achieved by the generally known methods and hence further description thereof will be omitted.

Upon the detection of the alignment of the noncontact tonometer with the top part of the cornea C on the basis of the output signals of the light receiving devices 52 and 65 at time t0, i.e., when an alignment completion signal is supplied at time t0, the arithmetic and control circuit 101 drives multiple light-emitting diodes 11 to be turned on. Light beams emitted by the light-emitting diodes 11 travel through the optically transparent parts of the ring pattern and fall on the cornea C of the eye E. Reflected light beams reflected from the cornea C travel through the objective lens 21, the semitransparent mirror 44, the telecentric diaphragm 22, the image forming lens 23 and the semitransparent mirror 51, and fall on the CCD 24. The image of the anterior segment of the eye E and an image of the ring pattern are formed on the CCD 24. An image signal supplied by the CCD 24 is transferred through the A/D converter 102 to the arithmetic and control circuit 101. The arithmetic and control circuit 101 stores sample image data on the images of the anterior segment of the eye E and the ring pattern sampled in a period between time t1 and time t2 when an operation for blowing an air pulse against the cornea C is started as first image data in the memory 103.

The arithmetic and control circuit 101 starts compressing air contained in the cylinder 31 at the time t2 by actuating the solenoid 33 to drive the piston 32. The air pressure Ap in the cylinder 31 increases substantially in proportion to time as shown in FIG. 7 and reaches a peak of 5 mmHg at time t4.

The arithmetic and control circuit 101 samples image data on the images of the anterior segment of the eye E and the ring pattern, which are input from the CCD 24, at time t3 T seconds after the time t2 when the operation for blowing an air pulse against the cornea C is started, and slightly before the time t4 and transfers the sampled image data as second image data to store the data in the memory 103.

After the second image data on the images of the anterior segment of the eye E and the ring pattern are thus stored in the memory 103, the arithmetic and control circuit 101 compares the data on the ring pattern with the reference data on ring patterns as shown in FIGS. 9($a$), 9($b$), 9($c$) and 9($i$) for pattern matching. The arithmetic and control circuit 101 selects one of the reference data representing a ring pattern that is the most analogous with the ring pattern and makes the display 200 display an intraocular tension corresponding to the selected reference data. For example, the arithmetic and control circuit 101 makes the display 200 display information indicating that the intraocular tension of the eye E is 10 mmHg, 15 mmHg or P mmHg if the image of the ring pattern represented by the second image data stored in the memory 103 coincides with the image of the ring pattern shown in FIG. 9($a$), FIG. 9($b$) or FIG. 9($i$).

The arithmetic and control circuit 101 calculates the radius of curvature of the cornea C on the basis of the image of the ring pattern represented by the first image data stored in the memory 103, and uses the results of calculation for correcting the intraocular tension determined by pattern matching.

A ring pattern of a single ring or a pattern similar to a bar code may be used instead of the ring pattern consisting of the plurality of concentric rings.

(2) Second Embodiment

The noncontact tonometer in the first embodiment measures the deformation of the cornea C of the eye E by the foregoing method comprising projecting the light pattern on the anterior segment of the eye E by the Placido's ring pattern projecting system on the eye E, blowing an air pulse against the cornea C, and measuring the deformed light pattern represented by reflected light. The deformation of the cornea C may be measured by any suitable method other than the foregoing method.

Figure 10:
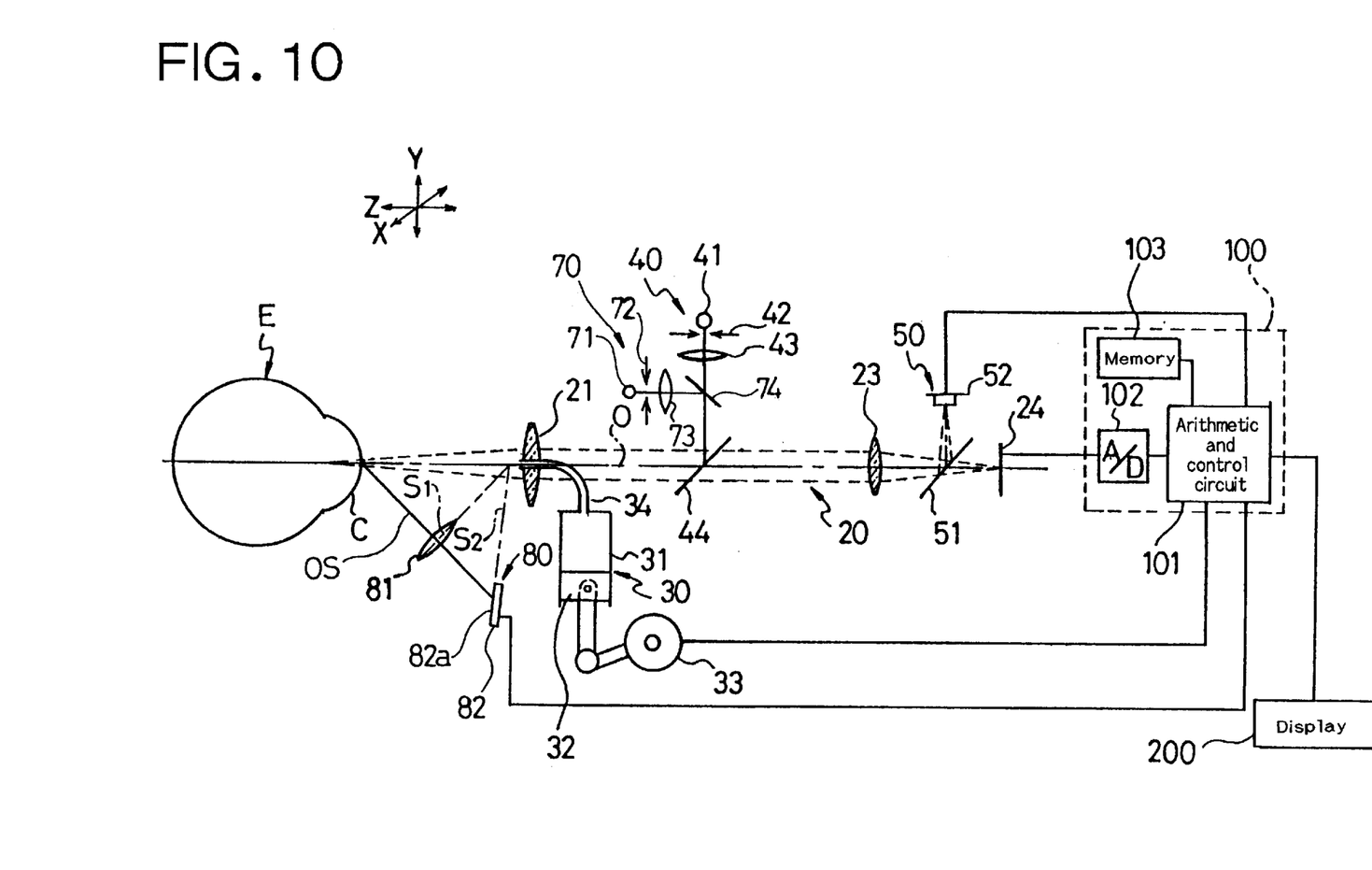
FIG. 10 is a block diagram of an optical system and a control system included in a noncontact tonometer in a second embodiment according to the present invention.

For example, a change in the shape of a section of the cornea of the eye caused by blowing air against the cornea may be measured by an optical system based on Scheinplug's principle. A noncontact tonometer in the second embodiment is not provided with any components corresponding to the Placido's ring pattern projecting system 10 and the telecentric diaphragm 22 shown in FIG. 4. As shown in FIG. 10, the noncontact tonometer in the second embodiment comprises a slit illuminating system 70 and a anterior segment section photographing system 80. A section of the cornea C of the eye E is photographed by the slit illuminating system 70 and the anterior segment section photographing system 80. The noncontact tonometer measures a change in the shape of a section of the cornea C caused by air blown against the cornea C by photographing the section of the cornea C by the slit illuminating system 70 and the anterior segment section photographing system 80 before and after blowing air against the cornea C.

The slit illuminating system 70 shapes illuminating light emitted by an infrared light source 71 by a slit formed in a slit plate 72 in a slit light beam, collimates the slit light beam by a collimator lens 73, and projects the collimated light beam through a semitransparent mirror 74 and 44 and an objective lens 21 on the cornea C.

The anterior segment section photographing system 80 receives through an image forming lens 81 the slit light beam projected by the slit illuminating system 70 and reflected from the cornea C by an infrared-sensitive area CCD 82 (image sensing means). The CCD 82 has a light receiving surface inclined to the optical axis OS of the image forming lens 81. In this embodiment, the inclination of the surface of the CCD 82 to the optical axis OS is 45°. The slit plate 72, the image forming lens 81 and the CCD 82 are disposed so that an extension of an optical section of an image of the slit of the slit plate 72, the principal plane S1 of the image forming lens 81 and an extension S2 of the image forming surface 82$a$ of the CCD 82 meet each other on a single line of intersection.

A memory 103 stores reference image data on the images of the Placido's ring pattern formed when an air pulse of 5 mmHg in peak pressure (hereinafter referred to as "5 mmHg air pulse") is jetted against eyes respectively having known intraocular tensions. For example, sectional shape data, not shown, on the shapes of sections of corneas when an 5 mmHg air pulse is jetted against eyes respectively having intraocular tensions of 10+i mmHg (i=1, 2, 3, . . . and 10) is stored in the memory 103.

The operation of the noncontact tonometer will be described below.

When photographing a section of the cornea C, the noncontact tonometer is aligned with the cornea C with respect to directions along the X-axis and the Y-axis. The noncontact tonometer is positioned roughly relative to the cornea C with respect to directions along the Z-axis with reference to images displayed on a display 200. An arithmetic and control circuit 101 turns on an illuminating light source 71 to project the slit light beam on the cornea C.

After the noncontact tonometer has been aligned with the cornea C, the arithmetic and control circuit 101 forms an image of a section of the cornea C on the area CCD 82 in a period between time t1 and time t2 (FIG. 7) when an air jetting operation is started. An image signal supplied by the area CCD 82, i.e., first image data, is transferred through the arithmetic and control circuit 101 and stored in the memory 103.

The arithmetic and control circuit 101 starts compressing air contained in a cylinder 31 at the time t2 (FIG. 7) by actuating a solenoid 33 to drive a piston 32. The air pressure Ap in the cylinder 31 increases substantially in proportion to time as shown in FIG. 7 and reaches a peak of 5 mmHg at time t4.

The arithmetic and control circuit 101 makes the area CCD 82 form a section of the cornea C at time t3 T seconds after the time t2 when the operation for blowing an air pulse against the cornea C is started, and slightly before the time t4 when the pressure of an air pulse reaches the maximum. Then, an image signal supplied by the area CCD 82 is transferred through the arithmetic and control circuit 101 and is stored as second image data in the memory 103 stores.

Subsequently, the arithmetic and control circuit 101 makes the display 200 display superposed images of the sectional shapes of the cornea C represented by the first image data and the second image data stored in the memory 103.

The arithmetic and control circuit 101 reads sequentially the reference data stored in the memory 103, compares the images of the sectional shapes of the cornea C represented by the first and the second image data with the reference data. The arithmetic and control circuit 101 selects one of the reference data representing a reference sectional shape that is the most analogous with the sectional shape, and makes the display 200 display an intraocular tension corresponding to the selected reference data.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. A noncontact tonometer comprising: an air current blowing means for blowing an air current against an eye; and a cornea deformation measuring means for optically measuring a deformation of the cornea caused by the air current blowing means;

wherein said cornea deformation measuring means comprises:

a light pattern projecting system which projects a light pattern on the eye;

a light receiving system which receives a reflected light pattern reflected from the cornea; and an arithmetic means which calculates intraocular tension of the eye on the basis of a change in a shape of an image of the light pattern formed on the light receiving system.

2. The noncontact tonometer according to claim 1, wherein the arithmetic means calculates the intraocular tension of the eye on the basis of degree of deformation of the image of the light pattern in a predetermined time.

3. The noncontact tonometer according to claim 1, wherein the light pattern consists of a plurality of concentric rings having their centers on the optical axis of the eye.

4. The noncontact tonometer according to claim 1, wherein the air current blowing means comprises an air blowing means capable of blowing an air current of a pressure lower than that necessary for the applanation of the cornea of the eye.

5. The noncontact tonometer according to claim 1, wherein the light receiving system is telecentric with respect to the side of an object.

6. The noncontact tonometer according to claim 1 further comprising a memory for storing reference data to be used for determining the intraocular tension of the eye, wherein the arithmetic means compares an image of a pattern formed by the light receiving system with the reference data and calculates the intraocular tension of the eye on the basis of the results of comparison.

7. The noncontact tonometer according to claim 1, wherein the cornea deformation measuring means comprises an image forming means capable of forming an image of a section of an anterior segment of the eye, and the arithmetic means calculates the intraocular tension of the eye on the basis of the image of the section formed by the image forming means.

* * * * *